US010450245B2

United States Patent
Gorawara et al.

(10) Patent No.: US 10,450,245 B2
(45) Date of Patent: Oct. 22, 2019

(54) PROCESS FOR PURIFYING HYDROCARBON STREAMS USING LOW REACTIVITY ADSORBENTS

(71) Applicant: UOP LLC, Des Plaines, IL (US)

(72) Inventors: Jayant K. Gorawara, Buffalo Grove, IL (US); Jason L. Noe, Mount Prospect, IL (US); Vladislav I. Kanazirev, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 15/789,914

(22) Filed: Oct. 20, 2017

(65) Prior Publication Data

US 2018/0057427 A1    Mar. 1, 2018

Related U.S. Application Data

(63) Continuation of application No. PCT/US2016/052992, filed on Sep. 22, 2016.

(60) Provisional application No. 62/222,326, filed on Sep. 23, 2015.

(51) Int. Cl.

| | | |
|---|---|---|
| *C07C 7/13* | (2006.01) |
| *B01J 20/04* | (2006.01) |
| *B01J 20/08* | (2006.01) |
| *B01J 20/18* | (2006.01) |
| *B01D 53/02* | (2006.01) |
| *C10G 25/05* | (2006.01) |
| *C10G 25/00* | (2006.01) |
| *B01D 3/40* | (2006.01) |
| *B01D 53/04* | (2006.01) |
| *C07C 7/00* | (2006.01) |
| *C07C 7/08* | (2006.01) |
| *C10G 7/00* | (2006.01) |
| *B01J 20/06* | (2006.01) |
| *B01J 20/12* | (2006.01) |
| *B01J 20/28* | (2006.01) |
| *B01J 20/30* | (2006.01) |
| *B01J 20/34* | (2006.01) |
| *B01J 20/10* | (2006.01) |

(52) U.S. Cl.
CPC ............... *C07C 7/13* (2013.01); *B01D 3/40* (2013.01); *B01D 53/02* (2013.01); *B01D 53/04* (2013.01); *B01J 20/04* (2013.01); *B01J 20/06* (2013.01); *B01J 20/08* (2013.01); *B01J 20/103* (2013.01); *B01J 20/12* (2013.01); *B01J 20/18* (2013.01); *B01J 20/186* (2013.01); *B01J 20/2803* (2013.01); *B01J 20/28042* (2013.01); *B01J 20/3007* (2013.01); *B01J 20/3078* (2013.01); *B01J 20/3408* (2013.01); *B01J 20/3458* (2013.01); *C07C 7/005* (2013.01); *C07C 7/08* (2013.01); *C10G 7/00* (2013.01); *C10G 25/003* (2013.01); *C10G 25/05* (2013.01); *B01D 2253/1085* (2013.01); *B01D 2253/112* (2013.01); *B01D 2256/24* (2013.01); *B01D 2257/20* (2013.01); *B01D 2257/304* (2013.01); *B01D 2257/306* (2013.01); *B01D 2257/308* (2013.01); *B01D 2257/504* (2013.01); *B01D 2257/553* (2013.01); *B01D 2257/704* (2013.01); *Y02C 10/08* (2013.01)

(58) Field of Classification Search
CPC .. C07C 7/005; C07C 7/08; C07C 7/13; C10G 7/00; C10G 25/003; C10G 25/05; B01J 20/04; B01J 20/0608; B01J 20/12; B01J 20/18; B01J 20/103; B01J 20/186; B01J 20/2803; B01J 20/3007; B01J 20/3078; B01J 20/3408; B01J 20/3458; B01J 20/28042; B01D 53/02; B01D 53/04; B01D 3/40; B01D 2256/24; B01D 2257/306; B01D 2257/504; B01D 2257/704; B01D 2253/112; B01D 2253/1085; B01D 2257/20; B01D 2257/304; B01D 2257/308; B01D 2257/553; Y02C 10/08
See application file for complete search history.

(56) References Cited

U.S. PATENT DOCUMENTS

| | | |
|---|---|---|
| 2,883,244 A | 4/1959 | Hugo |
| 2,915,365 A | 12/1959 | Fernand |
| 3,130,007 A | 4/1964 | Breck |
| 3,862,900 A | 1/1975 | Reusser |
| 4,503,023 A | 3/1985 | Breck et al. |

(Continued)

FOREIGN PATENT DOCUMENTS

| | | |
|---|---|---|
| CN | 103611495 A | 3/2014 |
| CN | 102676207 B | 12/2014 |

OTHER PUBLICATIONS

Broadhurst, "Removal of chloride compounds", Petrochemicals and Gas Processing, Petroleum Technology Quarterly, (2003) vol. 8 (3), p. 127-135.

(Continued)

*Primary Examiner* — Brian A McCaig
*Assistant Examiner* — Jason Y Chong

(57) ABSTRACT

This present disclosure relates to processes for removing contaminants from hydrocarbon streams, e.g. removing chlorides, $CO_2$, COS, $H_2S$, $AsH_3$, methanol, mercaptans and other S- or O-containing organic compounds from olefins, paraffins, aromatics, naphthenes and other hydrocarbon streams. The process involves contacting the stream with an adsorbent which comprises a zeolite, an alumina component and a metal component e.g. sodium, in an amount at least 30% of the zeolite's ion exchange capacity.

13 Claims, No Drawings

(56) References Cited

U.S. PATENT DOCUMENTS

| | | | | |
|---|---|---|---|---|
| 4,789,457 A | * | 12/1988 | Fischer | C10G 47/16 |
| | | | | 208/111.3 |
| 4,955,468 A | * | 9/1990 | Lee | B01D 3/40 |
| | | | | 203/14 |
| 5,107,061 A | * | 4/1992 | Ou | A62D 3/34 |
| | | | | 585/642 |
| 5,620,589 A | | 4/1997 | Yan | |
| 7,115,154 B1 | | 10/2006 | Kanazirev | |
| 8,551,328 B2 | | 10/2013 | Maglio et al. | |
| 8,771,501 B2 | | 7/2014 | Cosyns et al. | |
| 2002/0147377 A1 | | 10/2002 | Kanazirev | |

OTHER PUBLICATIONS

Search Report dated Jan. 12, 2017 for corresponding PCT Appl. No. PCT/US2016/052922.

* cited by examiner

PROCESS FOR PURIFYING HYDROCARBON STREAMS USING LOW REACTIVITY ADSORBENTS

CROSS-REFERENCE TO RELATED APPLICATIONS

This application is a Continuation of copending International Application No. PCT/US2016/052992 filed Sep. 22, 2016 which application claims benefit of U.S. Provisional Application No. 62/222,326 filed Sep. 23, 2015, the contents of which cited applications are hereby incorporated by reference in their entirety.

FIELD

This present disclosure relates to processes for removing contaminants from hydrocarbon streams, e.g. removing chlorides, $CO_2$, COS, $H_2S$, $AsH_3$, methanol, mercaptans and other S- or O-containing organic compounds from olefins, paraffins, aromatics, naphthenes and other hydrocarbon streams. The process involves contacting the stream with an adsorbent which comprises a zeolite, a binder, and a metal component e.g. sodium, in an amount at least 30% of the zeolite's ion exchange capacity.

BACKGROUND

Solid adsorbents are commonly used to remove contaminants from hydrocarbon streams such as olefins, natural gas and light hydrocarbon fractions. Since these streams can contain different contaminants, more than one adsorbent or adsorbent bed may be needed to sufficiently purify the stream so that it can be used in the desired process. Contaminants which can be present in these streams include chlorides, $H_2O$, CO, $O_2$, $CO_2$, COS, $H_2S$, $NH_3$, $AsH_3$, $PH_3$, Hg, methanol, mercaptans and other S- or O-containing organic compounds.

Aromatics extraction units which may accept a feed for a continuous catalytic reforming platforming unit may have corrosion problems caused by chloride ingress and accumulation of chlorides in the solvent. Current methods for chloride removing using solid adsorbents is practiced in the art, however it is an expensive option because a large heavy hydrocarbon containing stream must be treated in order for the method to be effective.

For example, a refiner extracting benzene from a reformed stream may apply a chloride removal bed on the feed to the benzene extraction unit. The chloride removal bed may be applied since chlorides in the feed to the unit may have been contributing to corrosion issues in the unit. However, once the chloride removal bed was applied to the feed, the corrosion issues of the unit were improved as indicated by the pH control of the process streams, more specifically, areas of acidity were greatly improved. Using this placement, over time the unit begins to have problems with recovery of the benzene. The poor recovery of benzene is assigned to a buildup of heavy oil in the solvent of the unit causing the solvent to be less effective. The adsorbent acts as a catalyst for acid catalyzed reactions such as alkylation of aromatic hydrocarbons with olefins. The catalytic action of the adsorbent is even more enhanced upon adsorption of chloride contaminants. The side reaction of alkylation described above leads to substantial increase of the molecular weight of the feeds, sometimes by factor of two or more. This high molecular weight material built up in the unit is detrimental as the unit is not designed to handle this material.

Therefore, there is a need for a process using a reasonably sized and properly located chloride removal bed.

SUMMARY

A first embodiment of the invention is a process for removing contaminants from hydrocarbon streams comprising contacting the hydrocarbon stream comprising olefins, paraffins, aromatics, naphthenes having a boiling point of about 50° C. to about 180° C., preferably about 50° C. to about 115° C. with an adsorbent at adsorption conditions to remove a portion of at least one chloride containing contaminant wherein the adsorbent comprising a zeolite component, a binder, and a metal component to produce a hydrocarbon product stream. An embodiment of the invention is one, any or all of prior embodiments in this paragraph up through the first embodiment in this paragraph, wherein the zeolite is selected from the group consisting of zeolite X, zeolite Y, zeolite A, and mixtures thereof. An embodiment of the invention is one, any or all of prior embodiments in this paragraph up through the first embodiment in this paragraph, wherein the binder is selected from the group consisting of alumina, silica, clay, alumina silicate, tinania, zirconia, and mixtures thereof. An embodiment of the invention is one, any or all of prior embodiments in this paragraph up through the first embodiment in this paragraph, wherein the zeolite is zeolite X. An embodiment of the invention is one, any or all of prior embodiments in this paragraph up through the first embodiment in this paragraph, wherein the adsorbent has a silica to alumina ratio of between about 2.0 to about 2.5, preferably about 2.1. An embodiment of the invention is one, any or all of prior embodiments in this paragraph up through the first embodiment in this paragraph, wherein the adsorption conditions include a temperature of about 50° C. to about 150° C., preferably about 120° C. An embodiment of the invention is one, any or all of prior embodiments in this paragraph up through the first embodiment in this paragraph, wherein the metal component is an alkali metal selected from the group consisting of sodium, potassium, lithium, rubidium, cesium, and mixtures thereof. An embodiment of the invention is one, any or all of prior embodiments in this paragraph up through the first embodiment in this paragraph, wherein the metal component is sodium. An embodiment of the invention is one, any or all of prior embodiments in this paragraph up through the first embodiment in this paragraph, wherein the zeolite is present in an amount from about 30 wt % to about 95 wt % of the adsorbent.

An embodiment of the invention is one, any or all of prior embodiments in this paragraph up through the first embodiment in this paragraph, further comprising sending the hydrocarbon product stream to an extractive distillation unit for the recovery of aromatics. An adsorbent for removing contaminants from hydrocarbon streams comprising a zeolite component, a binder component, and a metal component. The zeolite is selected from the group consisting of zeolite X, zeolite Y, zeolite A, and mixtures thereof. The binder is selected from the group consisting of alumina, silica, clay, alumina silicate, tinania, zirconia, and mixtures thereof. The adsorbent may have a silica to alumina ratio of between about 2.0 to about 2.5. The metal component may be a alkali metal selected from the group consisting of sodium, potassium, lithium, rubidium, cesium, and mixtures thereof. The zeolite may be present in an amount from about 30 wt % to about 95 wt % of the adsorbent.

Additional objects, advantages and novel features of the examples will be set forth in part in the description which follows, and in part will become apparent to those skilled in the art upon examination of the following description or may be learned by production or operation of the examples. The objects and advantages of the concepts may be realized and attained by means of the methodologies, instrumentalities and combinations particularly pointed out in the appended claims.

DEFINITIONS

As used herein, the term "stream", "feed", "product", "part" or "portion" can include various hydrocarbon molecules, such as straight-chain, branched, or cyclic alkanes, alkenes, alkadienes, and alkynes, and optionally other substances, such as gases, e.g., hydrogen, or impurities, such as heavy metals, and sulfur and nitrogen compounds. Each of the above may also include aromatic and non-aromatic hydrocarbons.

Hydrocarbon molecules may be abbreviated $C_1$, $C_2$, $C_3$, Cn where "n" represents the number of carbon atoms in the one or more hydrocarbon molecules or the abbreviation may be used as an adjective for, e.g., non-aromatics or compounds. Similarly, aromatic compounds may be abbreviated $A_6$, $A_7$, $A_8$, An where "n" represents the number of carbon atoms in the one or more aromatic molecules. Furthermore, a superscript "+" or "−" may be used with an abbreviated one or more hydrocarbons notation, e.g., $C_{3+}$ or $C_{3-}$, which is inclusive of the abbreviated one or more hydrocarbons. As an example, the abbreviation "$C_{3+}$" means one or more hydrocarbon molecules of three or more carbon atoms.

As used herein, the term "zone" can refer to an area including one or more equipment items and/or one or more sub-zones. Equipment items can include, but are not limited to, one or more reactors or reactor vessels, separation vessels, distillation towers, heaters, exchangers, pipes, pumps, compressors, and controllers. Additionally, an equipment item, such as a reactor, dryer, or vessel, can further include one or more zones or sub-zones.

As used herein, the term "silica to alumina ratio" can refer to the molar ratio of silicon oxide ($SiO_2$) and aluminum oxide ($Al_2O_3$) in the zeolite framework.

DETAILED DESCRIPTION

The following description is not to be taken in a limiting sense, but is made merely for the purpose of describing the general principles of exemplary aspects. The scope of the present disclosure should be determined with reference to the claims.

Applicant's invention comprises a purification process using a solid shaped adsorbent. With regard to the solid shaped adsorbent, one necessary component may be a low reactivity binder. The binder may be high surface area, porous material, providing a binding matrix. The binder may be selected from the group consisting of alumina, silica, clay, alumina silicate, tinania, zirconia, and mixtures thereof. In one embodiment, the low reactivity binder may be an activated alumina. In another embodiment, the low reactivity binder may be a clay. Activated aluminas include aluminas having a surface area usually greater than 100 $m^2/g$ and typically in the range of 100 to 400 $m^2/g$. Further, the activated alumina powder is preferably obtained by rapid dehydration of aluminum hydroxides, e.g., alumina trihydrate in a stream of hot gasses or solid heat carrier. Dehydration may be accomplished in any suitable apparatus using the stream of hot gases or solid heat carrier. Generally, the time for heating or contacting with the hot gases is a very short period of time, typically from a fraction of a second to 4 or 5 seconds. Normally, the temperature of the gases varies between 400° and 1000° C. The process is commonly referred to as flash calcination and is disclosed, for example in U.S. Pat. No. 2,915,365, incorporated herein by reference. However, other methods of calcination may be employed.

The activated aluminas suitable for use in the present invention have a median particle size in the range of 0.1 to 300 microns, preferably 1 to 100 microns and typically 1 to 20 microns. In certain instances, it may be desirable to use aluminas with a median particle size of 1 to 10 microns. The alumina may be ground to the desired particle size before or after activation. The activated alumina typically has an LOI (loss on ignition) in the range of about 5 to 12% at a temperature of 200° to 1000° C. One source of activated alumina is gibbsite which is one form of alumina hydrate derived from bauxite using the Bayer process. However, alpha alumina monohydrate, pseudoboehmite or the alumina trihydrate may be used if sufficiently calcined. Other sources of alumina may also be utilized including clays and alumina alkoxides.

The clay suitable for use in the present invention may include high purity clays having small particle size. The binding properties of the clays are very well known in the art. Typically, clays a naturally occurring, fine grained minerals like kaolinite, halloysite, illite and montmorilonite. Other clays group include smelctite, sepiolite, attapulgite, chlorite and others. By composition clays are sheet like aluminosilicates. The application of binders is highly dependent on their purity and binding properties. The low reactivity of the binder is a critical property for the purpose of this invention. The clay binder must not act as catalyst with respect of all components of the hydrocarbon feed.

Another necessary component of the present invention is a zeolite. Zeolites are crystalline aluminosilicate compositions which are microporous and which have a three-dimensional oxide framework formed from corner sharing $AlO_2$ and $SiO_2$ tetrahedra. Zeolites are characterized by having pore openings of uniform dimensions, having a significant ion exchange capacity, and being capable of reversibly desorbing an adsorbed phase which is dispersed throughout the internal voids of the crystal without significantly displacing any atoms which make up the permanent zeolite crystal structure. The zeolites which can be used in the present invention are those which have a pore opening of about 5 to about 10 Å.

In general, the zeolites have a composition represented by the empirical formula:

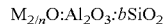

$$M_{2/n}O{:}Al_2O_3{:}bSiO_2$$

where M is a cation having a valence of "n" and "b" has a value of about 2 to about 500. Preferred zeolites are those that have a $SiO_2/Al_2O_3$ ratio of about 2:1 to about 6:1 and/or those having the crystal structure of zeolite X, faujasite, zeolite Y, zeolite A, mordenite, beta and ferrierite. Especially preferred zeolites are zeolites X, Y and A.

Preparation of these zeolites is well known in the art and involves forming a reaction mixture composed of reactive sources of the components which mixture is then hydrothermally reacted to form the zeolite. Specifically, the synthesis of zeolite Y is described in U.S. Pat. Nos. 3,130,007 and 4,503,023 and that of zeolite X in U.S. Pat. Nos. 2,883,244 and 3,862,900, the disclosures of which are incorporated by reference.

Although the synthesis of zeolites, and zeolites X and Y in particular, are well known, a brief description will be presented here for completeness. Reactive sources of M include without limitation the halide and hydroxide compounds of alkali or alkaline earth metals such as sodium chloride, sodium hydroxide, potassium hydroxide, etc. Aluminum sources include but are not limited to boehmite alumina, gamma alumina and soluble aluminates such as sodium aluminate or tetraethylammonium aluminates. Finally, silicon sources include, without limitation, silica, silica hydrosol, silicic acid, etc.

The reactive sources are combined into a reaction mixture which has a composition in terms of mole ratios of the oxides of:

$SiO_2/Al_2O_3 = 8$ to 12

$M_2O/Al_2O_3 = 2.5$ to 4

$H_2O/M_2O = 120$ to 180 and the mixture is then reacted to form the zeolite.

As synthesized, the zeolites will contain "M" metals in the channels and/or pores. The function of these metal cations is to balance the negative charge of the zeolite lattice. Since these cations are not part of the framework, they are exchangeable and are said to occupy exchange sites. The total amount of metal cations present in the zeolite is referred to as the stoichiometric amount or the maximum ion exchange capacity of the zeolite. This amount is usually expressed in moles.

Since the metal cations initially present in the zeolite are exchangeable they can be exchanged for other (different) alkali metals, alkaline earth metals, hydrogen ions, ammonium ions or mixtures thereof. If the zeolite to be used contains partially or completely hydrogen or ammonium ions, then these ions must be fully exchanged with alkali metals, alkaline earth metals or mixtures thereof, either before or during the preparation of the composite adsorbent.

Another necessary component of the shaped adsorbent of this invention is a metal component ($M_{add}$) selected from the group consisting of alkali, alkaline earth metals and mixtures thereof. This metal component ($M_{add}$) is in addition to the metal cation (M) present in the exchange sites of the zeolite. That is, the $M_{add}$ is present over and above the amount of exchangeable M metal ion present in the exchange sites of the zeolite. Additionally the $M_{add}$ metal can be the same or different than the M metal. For example, the M metal in a zeolite can be potassium whereas the $M_{add}$ can be sodium.

Specific examples of $M_{add}$ include but are not limited to sodium, potassium, lithium, rubidium, cesium, calcium, strontium, magnesium, barium, zinc and copper. The source of the (metal component precursor) can be any compound which at activation conditions, (see infra) decomposes to the metal oxide. Examples of these sources are the nitrates, hydroxides, carboxylates, carbonates and oxides of the metals. The shaped adsorbent can be prepared by combining the three components in any order and forming into a shaped article although not necessarily with equivalent results.

In one method, the alumina, zeolite and an aqueous solution of the desired metal compound are mixed and formed into a shaped article. For example, gamma alumina, zeolite X and a solution of sodium acetate can be combined into a dough and then extruded or formed into shapes such as pellets, pills, tablets or spheres (e.g. by the oil drop method) by means well known in the art. A preferred method of forming substantially rounded shapes or bodies involves the use of a pan nodulizer. This technique uses a rotating pan or pan nodulizer onto which is fed the alumina component, zeolite component and a solution of the metal component thereby forming substantially rounded articles or bodies.

Another method of forming the shaped article is to mix powders of the alumina, zeolite, clay and metal compound followed by formation of pellets, pills, etc. A third method is to combine the alumina and zeolite components (powders), form them into a shaped article and then impregnate the shaped article with an aqueous solution of the metal compound. The forming step is carried out by any of the means enumerated above.

Having obtained the shaped articles, they are cured or dried at ambient temperature up to about 200° C. for a time of about 5 minutes to about 25 hours. The shaped articles can be cured in batches e.g. bins or trays or in a continuous process using a moving belt. Once the shaped articles are cured, they are activated by heating the cured articles at a temperature of about 275° C. to about 600° C. for a time of about 5 to about 70 minutes. The heating can be done with the articles in a moving pan or in a moving belt where the articles are direct fired to provide the finished solid adsorbent.

The finished adsorbent can now be used to remove contaminants from various hydrocarbon streams. The streams which can be treated include but are not limited to hydrocarbon streams, especially those containing saturated and/or unsaturated hydrocarbons. Olefin stream such as ethylene, propylene and butylenes can be especially treated using the instant adsorbent. These streams will contain one or more of the following contaminants: chlorides, HCl, $H_2O$, CO, $O_2$, $CO_2$, COS, $H_2S$, $NH_3$, $AsH_3$, $PH_3$, Hg, methanol, mercaptans and other S- or O-containing organic compounds.

A first embodiment of the invention is a process for removing contaminants from hydrocarbon streams comprising contacting the hydrocarbon stream comprising olefins, paraffins, aromatics, naphthenes having a boiling point of about 50° C. to about 180° C., preferably about 50° C. to about 115° C. with an adsorbent at adsorption conditions to remove a portion of at least one chloride containing contaminant wherein the adsorbent comprising a zeolite component, and a metal component to produce a hydrocarbon product stream. An embodiment of the invention is one, any or all of prior embodiments in this paragraph up through the first embodiment in this paragraph, wherein the zeolite is selected from the group consisting of zeolite X, zeolite Y, zeolite A, and mixtures thereof. An embodiment of the invention is one, any or all of prior embodiments in this paragraph up through the first embodiment in this paragraph, wherein the zeolite is zeolite X.

An embodiment of the invention is one, any or all of prior embodiments in this paragraph up through the first embodiment in this paragraph, wherein the adsorbent has a silica to alumina ratio of between about 2.0 to about 2.5, preferably about 2.1. An embodiment of the invention is one, any or all of prior embodiments in this paragraph up through the first embodiment in this paragraph, wherein the adsorption conditions include a temperature of about 50° C. to about 150° C., preferably about 120° C. An embodiment of the invention is one, any or all of prior embodiments in this paragraph up through the first embodiment in this paragraph, wherein the metal component is an alkali metal selected from the group consisting of sodium, potassium, lithium, rubidium, cesium, and mixtures thereof. An embodiment of the invention is one, any or all of prior embodiments in this paragraph up through the first embodiment in this paragraph, wherein the metal component is sodium. An embodiment of the invention is one, any or all of prior embodiments in this paragraph up through the first embodiment in this paragraph, wherein the zeolite is present in an amount from about 30 wt % to about 95 wt % of the adsorbent. An embodiment of the invention is one, any or all of prior embodiments in this paragraph up through the first embodiment in this paragraph, further comprising sending the hydrocarbon product stream to an extractive distillation unit for the recovery of aromatics.

An adsorbent for removing contaminants from hydrocarbon streams comprising a zeolite component, and a metal component. The adsorbent, wherein the zeolite is selected from the group consisting of zeolite X, zeolite Y, zeolite A, and mixtures thereof. The adsorbent may have a silica to alumina ratio of between about 2.0 to about 2.5. The metal component is a alkali metal selected from the group consisting of sodium, potassium, lithium, rubidium, cesium, and mixtures thereof. Preferably, the metal component is sodium. Further, the zeolite is present in an amount from about 30 wt % to about 95 wt % of the adsorbent.

The hydrocarbon streams are purified by contacting the stream with the solid adsorbent at adsorption conditions. The contacting can be carried out in a batch or continuous process with continuous being preferred. The adsorbent can be present as a fixed bed, moving bed or radial flow bed with fixed bed being preferred. When a fixed bed is used, the feed stream can be flowed in an upflow or downflow direction, with upflow being generally preferred for liquid feeds. If a moving bed is used the feed stream flow can be either co-current or counter-current. Further, when a fixed bed is used, multiple beds can be used and can be placed in one or more reactor vessel. Adsorption conditions include a temperature of about ambient to about 80° C., a pressure of about atmospheric to about 100 atm. ($1.01 \times 10^4$ kPa) and a contact time which depends on whether the hydrocarbon stream is a liquid or gaseous stream. For a liquid stream the contact time expressed in terms of liquid hourly space velocity (LHSV) is from about 0.5 to about 10 $hr^{-1}$, while for a gaseous stream, the gas hourly space velocity varies from about 500 to about 10,000 $hr^{-1}$.

After a certain amount of time, which time depends on the concentration of contaminants, the size of the bed and the space velocity, the adsorbent will be substantially spent, i.e. has adsorbed an amount of contaminant(s) such that the level of contaminant in the purified stream is above an acceptable level. At this time, the adsorbent is removed and replaced with fresh adsorbent. The spent adsorbent can be regenerated by means well known in the art and then placed back on service. In a typical regeneration procedure, the adsorbent is first drained and depressurized followed by a cold purge with an inert stream. Next, a warm purge in a downflow direction at 80° to 150° C. removes the retained hydrocarbons from the bed. Finally, the temperature is slowly raised to 280° to 320° C. and held there for at least 2 hours and then cooled to ambient temperature.

The adsorbent may also be regenerated outside the adsorption bed. For example, the spent adsorbent may be transported offsite for regeneration. Typically, this procedure is conducted by hearing an inert and oxygen containing atmosphere in property designed ovens.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims. In the foregoing, all temperatures are set forth in degrees Celsius and, all parts and percentages are by weight, unless otherwise indicated.

Specific Embodiments

While the following is described in conjunction with specific embodiments, it will be understood that this description is intended to illustrate and not limit the scope of the preceding description and the appended claims.

A first embodiment of the invention is a process for removing contaminants from hydrocarbon streams comprising contacting the hydrocarbon stream comprising olefins, paraffins, aromatics, naphthenes having a boiling point of about 50° C. to about 180° C., preferably about 50° C. to about 115° C. with an adsorbent at adsorption conditions to remove a portion of at least one chloride containing contaminant wherein the adsorbent comprising a zeolite component, a binder, and a metal component to produce a hydrocarbon product stream. An embodiment of the invention is one, any or all of prior embodiments in this paragraph up through the first embodiment in this paragraph, wherein the zeolite is selected from the group consisting of zeolite X, zeolite Y, zeolite A, and mixtures thereof. An embodiment of the invention is one, any or all of prior embodiments in this paragraph up through the first embodiment in this paragraph, wherein the binder is selected from the group consisting of alumina, silica, clay, alumina silicate, titania, zirconia, and mixtures thereof. An embodiment of the invention is one, any or all of prior embodiments in this paragraph up through the first embodiment in this paragraph, wherein the zeolite is zeolite X. An embodiment of the invention is one, any or all of prior embodiments in this paragraph up through the first embodiment in this paragraph, wherein the adsorbent has a silica to alumina ratio of between about 2.0 to about 2.5, preferably about 2.1. An embodiment of the invention is one, any or all of prior embodiments in this paragraph up through the first embodiment in this paragraph, wherein the adsorption conditions include a temperature of about 50° C. to about 150° C., preferably about 120° C. An embodiment of the invention is one, any or all of prior embodiments in this paragraph up through the first embodiment in this paragraph, wherein the metal component is an alkali metal selected from the group consisting of sodium, potassium, lithium, rubidium, cesium, and mixtures thereof. An embodiment of the invention is one, any or all of prior embodiments in this paragraph up through the first embodiment in this paragraph, wherein the metal component is sodium. An embodiment of the invention is one, any or all of prior embodiments in this paragraph up through the first embodiment in this paragraph, wherein the zeolite is present in an amount from about 30 wt % to about 95 wt % of the adsorbent. An embodiment of the invention is one, any or all of prior embodiments in this paragraph up through the first embodiment in this paragraph, further comprising sending the hydrocarbon product stream to an extractive distillation unit for the recovery of aromatics.

A second embodiment of the invention is an adsorbent for removing contaminants from hydrocarbon streams comprising a zeolite component, a binder component, and a metal component. An embodiment of the invention is one, any or all of prior embodiments in this paragraph up through the second embodiment in this paragraph, wherein the zeolite is selected from the group consisting of zeolite X, zeolite Y, zeolite A, and mixtures thereof. An embodiment of the invention is one, any or all of prior embodiments in this paragraph up through the second embodiment in this paragraph, wherein the zeolite is zeolite X. An embodiment of the invention is one, any or all of prior embodiments in this paragraph up through the second embodiment in this paragraph, wherein the binder is selected from the group consisting of alumina, silica, clay, alumina silicate, titania, zirconia, and mixtures thereof. An embodiment of the invention is one, any or all of prior embodiments in this paragraph up through the second embodiment in this paragraph, wherein the adsorbent has a silica to alumina ratio of between about 2.0 to about 2.5. An embodiment of the invention is one, any or all of prior embodiments in this paragraph up through the second embodiment in this paragraph, wherein the metal component is a alkali metal selected from the group consisting of sodium, potassium, lithium, rubidium, cesium, and mixtures thereof. An embodiment of the invention is one, any or all of prior embodiments in this paragraph up through the second embodiment in this paragraph, wherein the metal component is sodium. An embodiment of the invention is one, any or all of prior embodiments in this paragraph up through the second embodiment in this paragraph, wherein the zeolite is present in an amount from about 30 wt % to about 95 wt % of the adsorbent.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for removing contaminants from a hydrocarbon stream comprising contacting the hydrocarbon stream comprising olefins, paraffins, aromatics, or naphthenes having a boiling point of about 50° C. to about 180° C. with an adsorbent at adsorption conditions to remove a portion of at least one chloride containing contaminant to produce a hydrocarbon product stream, wherein the adsorbent comprising a zeolite component, a binder, and a metal component, wherein the zeolite component comprises a zeolite having a composition represented by the empirical formula:

$$M_{2/n}O:Al_2O_3:bSiO_2$$

wherein M is a cation having a valence of "n" and "b" has a value of about 2 to about 500, wherein the binder is selected from the group consisting of alumina, silica, clay, alumina silicate, titania, zirconia, and mixtures thereof, wherein the metal component is selected from the group consisting of alkali metals, alkaline earth metals, and mixtures thereof, and wherein the metal component is in addition to the cation M present in ion exchange sites of the zeolite.

2. The process of claim 1, wherein the zeolite is selected from the group consisting of zeolite X, zeolite Y, zeolite A, and mixtures thereof.

3. The process of claim 2, wherein the zeolite is zeolite X.

4. The process of claim 1, wherein the adsorbent has a silica to alumina ratio of between about 2.0 to about 2.5.

5. The process of claim 1, wherein the adsorption conditions include a temperature of about 50° C. to about 150° C.

6. The process of claim 1, wherein the metal component is the alkali metal selected from the group consisting of sodium, potassium, lithium, rubidium, cesium, and mixtures thereof.

7. The process of claim 1, wherein the metal component is sodium.

8. The process of claim 1, wherein the zeolite is present in an amount from about 30 wt % to about 95 wt % of the adsorbent.

9. The process of claim 1, further comprising sending the hydrocarbon product stream to an extractive distillation unit for the recovery of aromatics.

10. A process for removing contaminants from a hydrocarbon stream comprising contacting the hydrocarbon stream comprising olefins, paraffins, aromatics, or naphthenes having a boiling point of about 50° C. to about 180° C. with an adsorbent at adsorption conditions to remove a portion of at least one chloride containing contaminant to produce a hydrocarbon product stream, wherein the adsorbent comprising a zeolite component, a binder, and a metal component, wherein the zeolite component has a pore opening of about 5 to about 10 Å, wherein the binder is selected from the group consisting of alumina, silica, clay, alumina silicate, titania, zirconia, and mixtures thereof, wherein the metal component is selected from the group consisting of alkali metals, alkaline earth metals, and mixtures thereof, and wherein the metal component is in addition to a cation present in ion exchange sites of the zeolite.

11. The process of claim 10, wherein the zeolite is selected from the group consisting of zeolite X, zeolite Y, zeolite A, and mixtures thereof.

12. The process of claim 10, wherein the adsorbent has a silica to alumina ratio of between about 2.0 to about 2.5.

13. The process of claim 10, wherein the zeolite is present in an amount from about 30 wt % to about 95 wt % of the adsorbent.

* * * * *